Figure 1:
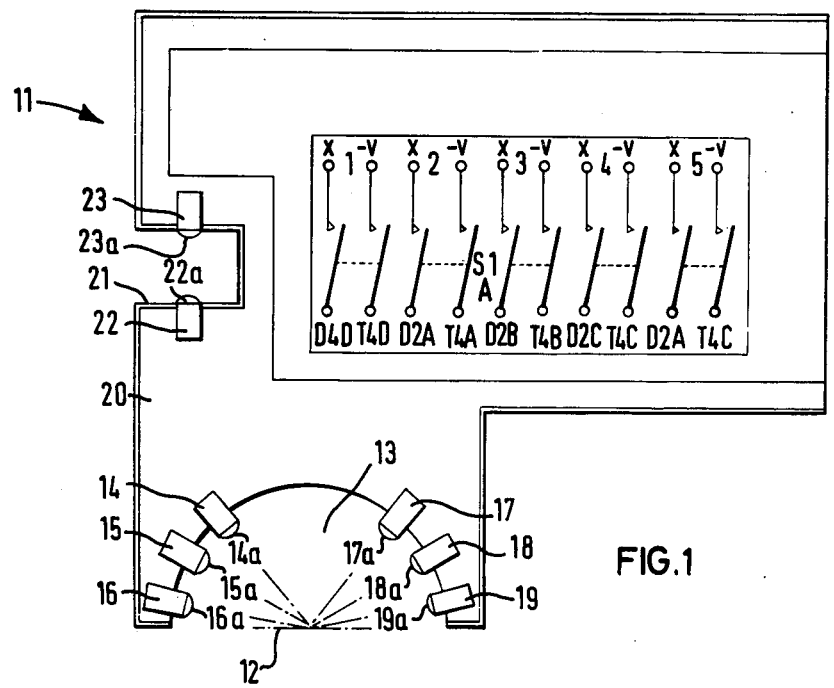

United States Patent [19]

Whitehouse et al.

[11] 4,218,144
[45] Aug. 19, 1980

[54] MEASURING INSTRUMENTS

[75] Inventors: David J. Whitehouse, Melton Mowbray; John Jungles, Thurmaston, both of England

[73] Assignee: The Rank Organisation Limited, London, England

[21] Appl. No.: 940,665

[22] Filed: Sep. 8, 1978

[30] Foreign Application Priority Data

Sep. 9, 1977 [GB] United Kingdom ............... 37709/77

[51] Int. Cl.² ............................................ G01N 21/48
[52] U.S. Cl. ................................. 356/446; 250/578; 356/445
[58] Field of Search .............................. 356/445–448; 250/578

[56] References Cited

U.S. PATENT DOCUMENTS 3,999,864  12/1976  Mutter .................................. 356/448

Primary Examiner—John K. Corbin
Assistant Examiner—Bruce Y. Arnold
Attorney, Agent, or Firm—Brisebois & Kruger

[57] ABSTRACT

An optical sensing instrument for detecting specular and/or non-specular reflections of light from a surface under test has a sensor head with a plane face having a semi-circular recess in which are housed a plurality of light sources and a plurality of photodetectors each having an associated lens, the optical axis of which passes through the center of curvature of the semi-circular recess. The photodetectors and the light sources are positioned such that respective source/detector pairs are located on optical axes which form mirror angles with respect to the axis of symmetry of the sensing head. Means are provided for simultaneously energizing one or more selected light sources and one or more of the photodetectors.

10 Claims, 2 Drawing Figures

MEASURING INSTRUMENTS

DESCRIPTION

The present invention relates to an optical sensing instrument, and particularly to such an instrument for detecting specular reflection of a surface under test.

Present day instruments for sensing specular reflection of surfaces under test suffer from various disadvantages and constraints, both of a mechanical and an electrical nature. The mechanical constraints arise from the need for such an instrument to have a measuring head which is required to work mostly at very low angles of incidence and reflection. The implication of this is that the physical size of the radiation emitter and detector of the assembly are usually between 10 and 100 times larger than the surface cross-section being sensed. This disparity leads consequently to the problem of radiation loss and lack of sensitivity. Systems involving mirrors and light guides have been tried, but also suffer from similar limitations as well as the added complexity of the light guiding arrangements.

The present invention is intended to provide an optical sensing instrument in which the disadvantages of previously known sensing instruments of the general type referred to, that is, instruments which operate by directing a beam of light at a surface under test and detecting the specular reflection, are largely overcome, or at least substantially reduced.

When used in the specification the term "light" will be understood to refer to electro-magnetic radiation which is not necessarily within the visible spectrum.

According to the present invention there is provided an optical sensing instrument having a sensing head carrying a plurality of light sources each having an associated lens, and a plurality of photodetectors each having an associated lens the angle between the optical axis of each lens associated with a photodetector and an axis of the sensing head being equal and opposite to the angle between the optical axis of the respective lens associated with a respective light source and the axis of the sensing head.

In one embodiment of the invention there are three light sources with associated lenses and three photodetectors all positioned such that respective source/detector pairs are located on optical axes which form mirror angles with respect to the axis of symmetry of the sensing head.

Apparatus according to the present invention may be used for measuring the specular reflection from rough surfaces. It is known that for a surface of roughness "h" (where h is the roughness of the surface having an R.M.S. value in either metric or imperial units as measured by a stylus instrument) the intensity of the light received at the angle of specular reflection varies as the function of the angle of incidence by the relationship:

$$I = k \exp(-4\pi h/\lambda \cos \alpha)^2)$$

where $\alpha$ is the angle of incidence and k is a constant depending on the reflection properties of the surface. The specular backscatter angle is that which lies at the same angle as the incident light from the normal. When the values of incident light intensity are plotted for different values of $h/\lambda$ corresponding to surfaces of different roughness, for example smooth, medium and rough surfaces, the curves so generated are approximately hyperbolic and a "knee" in each curve where the intensity variation rises rapidly for a small change in angle. This corresponds to the phenomenon of sheen gloss. Optical sensing instruments formed as embodiments of the present invention can be used in such a way that different light sources and/or photo detectors can be selected so that the angle of incident light on a surface under test can be varied: By selecting different light sources for operation, the variation of this angle enables the specular light reflected from a surface to be located on any desired point on the response curve.

Preferably, therefore, there are further provided in embodiments of the present invention, switching means operable such that a selected one or any selected combination of light sources and photo detectors can be energised. The energisation of the selected light source or group of light sources may be via a pulse generating system and in such an embodiment there is preferably provided a pulse detector system for providing an output signal from the pulses generated by the photo detectors; such an output signal may be a d.c. voltage suitable for feeding to a display device such as a meter.

The response curve of any specular reflection system is non-linear, and embodiments of the present invention can be provided with a pulse detector system including an amplifier circuit, the pulse detector and amplifier system having a non-linear response which can be adjusted to match different surface reflection characteristics. In other words, the approximately hyperbolic non-linear response to specular reflection can be compensated by utilising a non-linear pulse detector system having a non-linearity which varies in the opposite sense so that the eventual output is effectively linear.

There may further be provided a pulse integrating network operable to provide a linear relationship between input pulse height and a d.c. voltage output for feeding to a meter display.

In a practical embodiment of the invention the sensing head has a plane face with a recess which is part-circular in section taken on a plane normal to the said plane face, the said light sources and photo detectors being arranged in the recess such that the optical axes of their associated lenses all meet at the centre of curvature of the recess. For convenience the centre of curvature of the recess preferably lies in the plane of the said plane face so that this plane face can be positioned against a surface under test in order reliably to reproduce the illumination conditions experienced by the surface and detected by the photo detector.

Embodiments of the present invention may also be provided with means for taking measurements at incident angles of between 5° and 80° also may be provided with means for combining light source and photo detector pairs at angles which are not equal. This permits sensing to be effected in the special case of diffuse reflection as well as the specular reflection measuring capability. A sensing head may also contain a thickness or absorption sensitive system which can be energised by a suitable switch on the sensing head.

Because the device is sensitive to changes in proximity of the surface normal to the diametric plane of the sensing head the device may be used as a position or gauging sensor.

Figure 2:
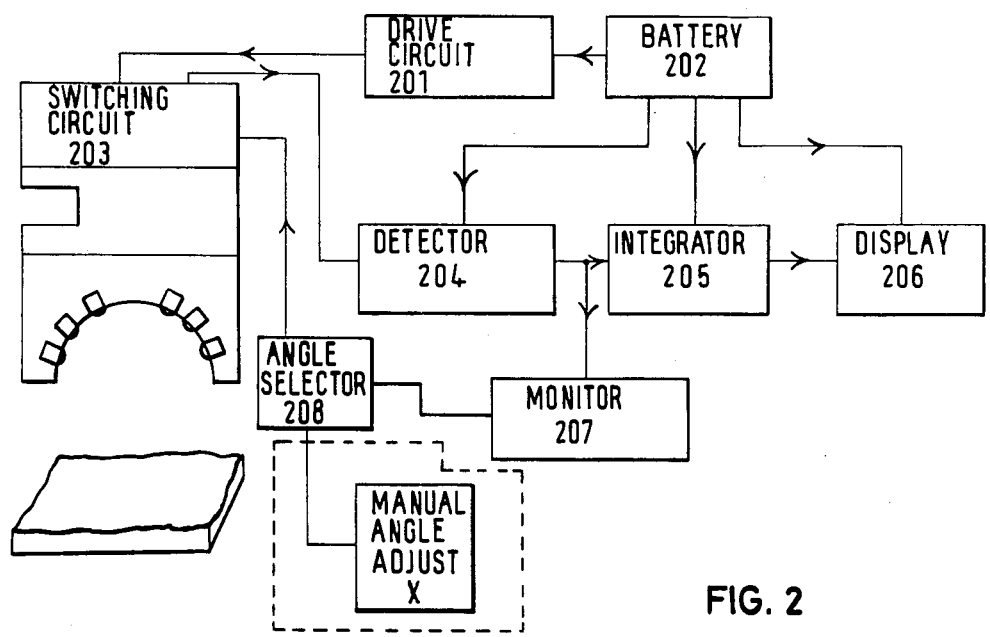

One embodiment of the present invention will now be more particularly described, by way of example, with reference to the accompanying drawings, in which:

FIG. 1 is a schematic view of a sensing head suitable for incorporation into an instrument formed as an embodiment of the invention; and FIG. 2 is a block schematic diagram of an instrument incorporating the sensing head of FIG. 1.

Referring now to FIG. 1 there is shown a sensing head generally indicated 11 of an optical sensing instrument having a plane work face 12 in which is formed a recess 13 which is semi-circular in section taken perpendicular to the plane of the surface 12, that is parallel to the plane of the paper. Mounted on the sensing head 11 are three gallium arsenide light emitting diodes 14, 15, 16, each having an associated lens 14a, 15a, 16a. The optical axis of the lenses 14a, 15a and 16a are all radial with respect to the semi-circular recess 13 and meet at the centre of curvature thereof.

Also mounted on the sensing head 11 are three photo detectors 17, 18, 19, having associated lenses 17a, 18a, 19a, the optical axes of which, like the lenses 14a, 15a, 16a, are all radial with respect to the recess 13 and co-incident at the centre of curvature thereof.

In another work face 20 of the sensing head 11, is a rectangular notch 21 having parallel sides in one of which is housed a light source 22 having an associated lens 22a and the other of which, aligned with the optical axis of the lens 22a is a photo detector 23 having an associated lens 23a. The associated light source and photo detector may be used for determining the thickness of translucent components by determining the intensity of light incident on the photo detector 23 after having passed through the material under test which is positioned in the notch 21.

Used in the reflectance mode the sensing head 11 is placed against the surface under test with the plane face 12 in contact therewith. Light from one or more of the light sources 14, 15, 16, is directed on the surface and reflected light detected by one or more of the sensors 17, 18, 19 as appropriate. The embodiment illustrated in FIG. 1 is in fact designed as a self-contained battery-driven portable sensing instrument and all the driving circuits and detection circuits are contained within the sensing head 11. As shown in FIG. 2 these circuits comprise a drive circuit 201 fed from a battery 202. The drive circuit 201 operates to generate drive pulses which are fed via a switching circuit 203 to a selected one or selected group of the light sources 14, 15, 16. The switching circuit 203 also operates to select which of the photodetectors 17, 18, 19 are energised and feeds output signals from the detectors to detector circuit 204 which is driven directly by the battery 202 and which feed output signals to an integrator 205 which feeds a display 206. The pulse integrating device 205 operates to provide a linear relationship between input pulse height and a D.C. voltage output for feeding to the display 206 which may, for example, be a meter. In the embodiment under discussion the light sources are gallium arsenide diodes and the drive circuit 201 incorporates pulse generating and amplifying circuits capable of driving one or all of the gallium arsenide diodes for small duty cycles. The pulse detector circuit 204 incorporates an amplifier system with a non-linear response which can be adjusted for matching to various functions of surface reflection characteristics. The switching circuit 203 can operate to select any combination of light source and photo-detector so that equal incident and reflected angles of light on the surface under test may be chosen, or scanned; or non-mirror angles may be utilised if diffuse reflection characteristics are being investigated.

A monitor circuit 207 is also provided, connected to the output of the detector circuit 204 and operable in response to the pulse height information, which can be suitably processed, to provide signals to control an automatic angle selector 208.

The automatic angle selector circuit 208 may be operated in response to information provided from outside the system (indicated by the block X within the broken outline) or may be driven with pre-programmed scanning sequences held within a memory incorporated within the device.

The available angles of incidence and reflection which can be utilised are, of course, predetermined by the number and position of the light sources and photodetectors, and this is fixed once the device has been manufactured. In use of the device a test surface of known specular reflection characteristics is positioned against the surface 12 and the light source driven in turn until the output intensity from the detectors starts to rise rapidly. At this point the "knee" of the system sensitivity has been passed and the output level on the meter is adjusted to read about 80% of the full scale. The instrument is then set up for detecting the surface roughness of other components of the same shape which can be compared with the original part of known characteristics by placing them against the surface 12. The output sensitivity of the instrument as indicated by the display 206 can then be used, without requiring any further adjustments to the instrument, to provide an immediate indication of the surface roughness. If any surface tested reflects a lower intensity of light it is rougher than the original test surface and can be rejected. On the other hand, if the original test surface were one having the greatest allowable smoothness, then rejection can be based on indications by the display which will represent a greater intensity of reflected light. In this case the original selection of the incident light angle would be again arranged to be over the "Knee" of the response curve but in this case the adjustment is made so that this corresponds to a 20% scale deflection. A higher intensity in reading then indicates a smoother surface and this can be rejected in dependence on given criteria.

What is claimed is:

1. In an optical sensing instrument for inspecting surfaces by detecting reflection therefrom at various different angles of incidence and reflection,
   a sensing head;
   means defining a plane in which a surface under test lies in use of said instrument;
   a plurality of light sources carried on said sensing head;
   a plurality of first lenses each associated with a respective one of said light sources, said first lenses directing light from their respective associated sources along respective optical axes towards a common area on said plane;
   a plurality of photodetectors mounted on said sensing head;
   a plurality of second lenses each associated with a respective one of said photodetectors for directing light reflected from a surface located at said plane to respective associated said photodetectors, the optical axis of each said first lens passing through said common area and lying at an angle, with respect to a normal to said plane, which is equal and opposite to the angle with respect to said normal formed by the axis of a respective one of said second lenses; and means for selecting which of said light sources and which of said photodetectors is to be energised at any one time during operation of said instrument.

2. In an optical sensing instrument, a sensing head;

a plurality of light sources carried on said sensing head;

a plurality of first lenses each associated with a respective one of said light sources, a plurality of photodetectors mounted on said sensing head;

a plurality of second lenses each associated with a respective one of said photodetectors, the optical axis of each of said first lens lying at an angle, with respect to an axis of said measuring head, which is equal and opposite to the angle with respect to said axis formed by the axis of a respective one of said second lenses; and switching means connected to said light sources and said photodetectors and operating to energise one of a selected one and any selected combination of light sources and detectors.

3. The optical sensing instrument of claim 1 or claim 2, wherein there is further provided:

a pulse generating system connected to said light sources and operating to drive at least one selected light source.

4. The optical sensing instrument of claim 3, wherein there is further provided:

a pulse detector system connected to said photodetectors and operating to provide an output signal in response to detection of pulses.

5. The optical sensing instrument of claim 4, wherein said pulse detector system includes an amplifier circuit, the system having a non linear response comprising said pulse detector and said amplifier, means for adjusting said non-linear response of said pulse detector and amplifier system to match with different surface reflectance characteristics.

6. The optical sensing instrument of claim 4, wherein there is further provided:

a meter display, and a pulse integrating network operating to provide a linear relationship between input pulse height and a D.C. voltage output for feeding to said meter display.

7. The optical sensing instrument of claim 1, wherein said sensing head has a plane face in which is formed a recess the shape of which, in section taken on a plane normal to said plane face, constitutes a part of a circle, said light sources and photodetectors being mounted in said recess so that the optical axes of said first and second lenses associated therewith all meet at the centre of curvature of said recess.

8. The optical sensing instrument of claim 7, wherein the centre of curvature of said recess lies in the plane of said plane face.

9. The optical sensing instrument of claim 2, wherein there are further provided means for energising a selected light source and at least one photodetector other than the one associated with the one of said second lenses the optical axis of which lies at an equal and opposite angle, with respect to said sensing head axis, to the one of said first lenses associated with said selected light source.

10. The optical sensing instrument of claim 5, wherein there is further provided;

a meter display, and a pulse integrating network operating to provide a linear relationship between input pulse height and a D.C. voltage output for feeding to said meter display.

* * * * *